United States Patent
Roth et al.

(10) Patent No.: US 6,984,764 B1
(45) Date of Patent: Jan. 10, 2006

(54) ALKYLAROMATICS PRODUCTION

(75) Inventors: Wieslaw J. Roth, Sewell, NJ (US);
Brian J. Ratigan, Philadelphia, PA (US); Dominick N. Mazzone, Wenonah, NJ (US)

(73) Assignee: ExxonMobil Oil Corporation, Houston, TX (US)

( * ) Notice: Subject to any disclaimer, the term of this patent is extended or adjusted under 35 U.S.C. 154(b) by 567 days.

(21) Appl. No.: 09/305,019

(22) Filed: May 4, 1999

(51) Int. Cl.
*C07C 2/02* (2006.01)
*C07C 2/66* (2006.01)

(52) U.S. Cl. ............... 585/323; 585/375; 585/467; 585/475

(58) Field of Classification Search ........... 585/323, 585/375, 467, 475
See application file for complete search history.

(56) References Cited

U.S. PATENT DOCUMENTS

| | | | |
|---|---|---|---|
| 3,751,504 A | 8/1973 | Keown et al. | 260/672 T |
| 3,766,093 A | 10/1973 | Chu | 252/455 Z |
| 3,894,104 A | 7/1975 | Chang et al. | 260/668 R |
| 4,016,218 A | 4/1977 | Haag et al. | 260/671 R |
| 4,547,605 A | 10/1985 | Kresege et al. | 585/467 |
| 4,891,458 A | 1/1990 | Innes et al. | 585/323 |
| 4,992,606 A | 2/1991 | Kushnerick et al. | 585/467 |
| 5,175,135 A | 12/1992 | Lee et al. | 502/64 |
| 5,243,116 A | 9/1993 | Lee et al. | 585/467 |
| 5,334,795 A | 8/1994 | Chu et al. | 585/467 |
| 5,453,554 A | 9/1995 | Cheng et al. | 585/467 |
| 5,557,024 A * | 9/1996 | Cheng et al. | 585/467 |
| 5,959,168 A | 9/1999 | Van der Aalst et al. | 585/323 |

FOREIGN PATENT DOCUMENTS

| | | |
|---|---|---|
| DE | 2558035 | 6/1977 |
| EP | 0733608 * | 9/1996 |
| WO | WO9814417 | 4/1998 |

* cited by examiner

*Primary Examiner*—Tam M. Nguyen
(74) *Attorney, Agent, or Firm*—Darryl M. Tyrus; Linda A. Kubena

(57) ABSTRACT

The present invention provides a process for producing a monoalkylated aromatic compound, particularly ethylbenzene or cumene, in which a polyalkylated aromatic compound is contacted with an alkylatable aromatic compound in the liquid phase and in the presence of a transalkylation catalyst comprising TEA-mordenite having an average crystal size of less than 0.5 micron.

9 Claims, No Drawings

ALKYLAROMATICS PRODUCTION

BACKGROUND OF THE INVENTION

The present invention relates to a process for producing alkylaromatics, particularly ethylbenzene and cumene.

Ethylbenzene and cumene are valuable commodity chemicals which are used industrially for the production of styrene monomer and phenol respectively. Ethylbenzene may be produced by a number of different chemical processes but one process which has achieved a significant degree of commercial success is the vapor phase alkylation of benzene with ethylene in the presence of a solid, acidic ZSM-5 zeolite catalyst. In the commercial operation of this process, the polyalkylated benzenes, including both polymethylated and polyethylated benzenes, which are inherently co-produced with ethylbenzene in the alkylation reactor, are transalkylated with benzene to produce additional ethylbenzene either by being recycled to the alkylation reactor or by being fed to a separate transalkylation reactor. Examples of such ethylbenzene production processes are described in U.S. Pat. No. 3,751,504 (Keown), U.S. Pat. No. 4,547,605 (Kresge), and U.S. Pat. No. 4,016,218 (Haag).

More recently focus has been directed at liquid phase processes for producing ethylbenzene from benzene and ethylene since liquid phase processes operate at a lower temperature than their vapor phase counterparts and hence tend to result in lower yields of by-products. For example, U.S. Pat. No. 4,891,458 describes the liquid phase synthesis of ethylbenzene with zeolite beta, whereas U.S. Pat. No. 5,334,795 describes the use of MCM-22 in the liquid phase synthesis of ethylbenzene.

Cumene has for many years been produced commercially by the liquid phase alkylation of benzene with propylene over a Friedel-Craft catalyst, particularly solid phosphoric acid or aluminum chloride. More recently, however, zeolite-based catalyst systems have been found to be more active and selective for propylation of benzene to cumene. For example, U.S. Pat. No. 4,992,606 describes the use of MCM-22 in the liquid phase alkylation of benzene with propylene.

U.S. Pat. No. 5,453,554 describes a process for producing short chain alkyl aromatic compounds, such as cumene and ethylbenzene, by contacting at least one alkylatable aromatic compound, such as benzene, with an alkylating agent having 1–5 carbon atoms in the presence of MCM-56. The process can be effected in either the liquid or vapor phase and polyalkyated by-products can be converted to additional monoalkylated product by transalkylation in the alkylation reactor or in a separate reactor. According to the '554 patent, the transalkylation catalyst can be MCM-49, MCM-22, PSH-3, SSZ-25, zeolite X, zeolite Y, zeolite beta or mordenite. Particular forms of mordenite cited in the '554 patent as suitable transalkylation catalysts are acid-dealuminized mordenite as disclosed in U.S. Pat. No. 5,243,116 and TEA-mordenite as disclosed in U.S. Pat. Nos. 3,766,093 and 3,894,104. Although U.S. Pat. Nos. 3,766,093 and 3,894,104 are silent as to the crystal size of the TEA-mordenite produced therein, a repeat of the Examples in these patents has shown the mordenite product to be predominantly large crystals with a size greater than 1 micron and typically around 5 to 10 micron.

One problem which exists in liquid phase processes for producing alkylaromatics, such as cumene and ethylbenzene, is that their lower operating temperatures increases the activity requirements of the catalyst particularly in the transalkylation step and an object of this invention is to provide an aromatics transalkylation catalyst of enhanced activity.

In particular, it has now unexpectedly been found that by producing TEA-mordenite with a controlled small crystal size of less than 0.5 micron, it is possible to produce a catalyst with materially enhanced activity for liquid phase aromatics transalkylation.

SUMMARY OF THE INVENTION

According to one aspect of the invention, there is provided a process for producing a monoalkylated aromatic compound comprising the step of contacting a polyalkylated aromatic compound with an alkylatable aromatic compound in the liquid phase and in the presence of a transalkylation catalyst comprising TEA-mordenite having an average crystal size of less than 0.5 micron to produce a monoalkylated aromatic compound.

Preferably, the alkyl groups of the polyalkylated aromatic compound have 1 to 5 carbon atoms.

In a further aspect, the invention resides in a process for producing a monoalkylated aromatic compound comprising the steps of:

(a) contacting an alkylatable aromatic compound with an alkylating agent in the presence of an alkylation catalyst to provide a product comprising said monoalkylated aromatic compound and a polyalkylated aromatic compound, and then (a) contacting the polyalkylated aromatic compound from step (a) with said alkylatable aromatic compound in the liquid phase and in the presence of a transalkylation catalyst comprising TEA-mordenite having an average crystal size of less than 0.5 micron to produce a monoalkylated aromatic compound.

Preferably, the alkylation step (a) is conducted in the liquid phase.

Preferably, the alkylating agent includes an alkylating aliphatic group having 1 to 5 carbon atoms.

Preferably, the alkylating agent is ethylene or propylene and the alkylatable aromatic compound is benzene.

Preferably, the alkylation catalyst of step (a) is selected from MCM-22, MCM49, MCM-56 and zeolite beta.

DETAILED DESCRIPTION OF THE INVENTION

The present invention relates to a process for the production of a monoalkylated aromatic compound, particularly ethylbenzene and cumene, by the liquid phase transalkylation of the polyalkylated derivative with an alkylatable compound, particularly benzene. More particularly, the invention is concerned with a process in which the liquid phase transalkylation step follows an alkylation step, which may also be carried out in the liquid phase and in which the alkylatable compound is reacted with an alkylating agent, particularly ethylene and propylene, to produce the required monoalkylated aromatic end product as well as the poly-alkylated derivative, which is separated and fed to the transalkylation step.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a hetero atom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such product are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_5$ to about $C_{12}$. When cumene or ethylbenzene is the desired product, the present process produces acceptably little by-products such as xylenes. The xylenes make in such instances may be less than about 500 ppm.

Reformate containing substantial quantities of benzene, toluene and/or xylene constitutes a particularly useful feed for the alkylation process of this invention.

The alkylating agents which are useful in the process of this invention generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mole % |
|---|---|---|
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products which may be obtained from the process of the invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes.

The alkylation process of this invention is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition, under effective alkylation conditions. Such conditions include a temperature of from about 0° C. to about 500° C., and preferably between about 50° C. and about 250° C., a pressure of from about 0.2 to about 250 atmospheres, and preferably from about 5 to about 100 atmospheres, a molar ratio of alkylatable aromatic compound to alkylating agent of from about 0.1:1 to about 50:1, and preferably can be from about 0.5:1 to about 10:1, and a feed weight hourly space velocity (WHSV) of between about 0.1 and 500 hr$^1$, preferably between 0.5 and 100 hr$^1$.

The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen.

When benzene is alkylated with ethylene to produce ethylbenzene, the alkylation reaction may be carried out in the liquid phase. Suitable liquid phase conditions include a temperature between 300° and 600° F. (about 1500 and 316° C.), preferably between 400° F. and 500° F. (about 205° C. and 260° C.), a pressure up to about 3000 psig (20875 kPa), preferably between 400 and 800 psig (2860 and 5600 kPa), a space velocity between about 0.1 and 20 WHSV, preferably between 1 and 6 WHSV, based on the ethylene feed, and a ratio of the benzene to the ethylene in the alkylation reactor from 1:1 to 30:1 molar, preferably from about 1:1 to 10:1 molar.

When benzene is alkylated with propylene to produce cumene, the reaction may also take place under liquid phase conditions including a temperature of up to about 250° C., e.g., up to about 150° C., e.g., from about 10° C. to about 125° C.; a pressure of about 250 atmospheres or less, e.g., from about 1 to about 30 atmospheres, and an aromatic hydrocarbon weight hourly space velocity (WHSV) of from about 5 hr$^1$ to about 250 hr$^1$, preferably from 5 hr$^1$ to 50 hr$^1$.

The alkylation catalyst is a crystalline molecular sieve preferably selected from MCM-22 (described in detail in U.S. Pat. No. 4,954,325), MCM-49 (described in detail in U.S. Pat. No. 5,236,575), MCM-56 (described in detail in U.S. Pat. No. 5,362,697), and zeolite beta (described in detail in U.S. Pat. No. 3,308,069). The molecular sieve can be combined in conventional manner with an oxide binder, such as alumina, such that the final alkylation catalyst contains between 2 and 80 wt % sieve.

The alkylation reactor effluent contains the excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the benzene distillation are further distilled to separate monoalkylated product from polyalkylated products and other heavies.

The polyalkylated products separated from the alkylation reactor effluent are reacted with additional aromatic feed in a transalkylation reactor over a suitable transalkylation catalyst. According to the invention, the transalkylation catalyst is a particular, small crystal form of TEA-mordenite, i.e., synthetic mordenite prepared from a reaction mixture comprising a tetraethylammonium directing agent. TEA mordenite is disclosed in U.S. Pat. Nos. 3,766,093 and 3,894,104 but, as will be demonstrated in the following Examples, the particular synthesis regimes described in these patents lead to the production of a mordenite product composed of predominantly large crystals with a size greater than 1 micron and typically around 5 to 10 micron. It has now been found that controlling the synthesis so that the resultant TEA-mordenite has an average crystal size of less than 0.5 micron results in a catalyst with materially enhanced activity for liquid phase aromatics transalkylation.

The required small crystal TEA-mordenite can be produced by crystallization from a synthesis mixture having a molar composition within the following ranges:

|  | Useful | Preferred |
|---|---|---|
| R/R + Na$^+$ = | >0.4 | 0.45–0.7 |
| OH$^-$/SiO$_2$ = | <0.22 | 0.05–0.2 |
| Si/Al$_2$ = | >30–90 | 35–50 |
| H$_2$O/OH = | 50–70 | 50–60 |

The crystallization is conducted at a temperature of 90 to 200° C., for a time of 6 to 180 hours. The resultant TEA-mordenite can be combined in conventional manner with an oxide binder, such as alumina, such that the final transalkylation catalyst contains between 2 and 80 wt % sieve.

The transalkylation reaction of the invention is conducted in the liquid phase under suitable conditions such that the polyalkylated aromatics react with the additional aromatic feed to produce additional monoalkylated product. Suitable transalkylation conditions include a temperature of 100 to 260° C., a pressure of 10 to 50 barg, a weight hourly space velocity of 1 to 10 on total feed, and benzene/polyalkylated benzene weight ratio 1:1 to 6:1.

When the polyalkylated aromatics are polyethylbenzenes and are reacted with benzene to produce ethylbenzene, the transalkylation conditions preferably include a temperature of 220 to 260° C., a pressure of 20 to 30 barg, weight hourly space velocity of 2 to 6 on total feed and benzene/PEB weight ratio 2:1 to 6:1.

When the polyalkylated aromatics are polypropylbenzenes and are reacted with benzene to produce cumene, the transalkylation conditions preferably include a temperature of 100 to 200° C., a pressure of 20 to 30 barg, weight hourly space velocity of 1 to 10 on total feed and benzene/PIPB weight ratio 1:1 to 6:1.

The effluent from the transalkylation reactor is blended with alkylation reactor effluent and the combined stream distilled to separate the desired monoalkylated product.

The invention will be described with reference to the following Examples and the accompanying drawing, which is a graph displaying conversion of diisopropylbenzene against time of reaction for the TEA-mordenite material of Example 1.

EXAMPLE 1

A synthesis mixture was prepared which comprised water, precipitated silica, aluminum sulfate solution, sodium hydroxide and tetraethylammonium bromide and which had the following molar composition (based alumina=1):
silica=39.7
Na$_2$O=7.3
SO$_4$$^=$=2.9
TEA=12.3
water=370

The synthesis mixture was crystallized at 149° C. (300° F.) with stirring at 90 RPM for 40–44 hrs. The resultant TEA-mordenite was isolated by filtration, washed and dried and found to have a crystal size by scanning electron microscopy of <0.5 micron.

EXAMPLE 2 (COMPARATIVE)

TEA-Mordenite material was prepared according to Example 10 from U.S. Pat. No. 4,052,472 from a synthesis mixture having the following molar composition: 30 SiO$_2$, 1 Al$_2$O$_3$, 7.5 Na$_2$O, 6.3 TEA (bromide) and 310 H$_2$O. The synthesis mixture was crystallized (with stirring at 200 RPM) at 174° C. (345° F.) for 72 hours. The resultant TEA-mordenite was isolated by filtration, washed and dried and found to have a predominant crystal size by scanning electron microscopy of >5 micron.

EXAMPLE 3 (COMPARATIVE)

TEA-Mordenite material was prepared according to Example 8 from U.S. Pat. No. 3,766,093, except that sodium aluminate solution containing 25.5% Al$_2$O$_3$ and 19.5% Na$_2$O was used. The synthesis mixture had the following molar composition: 30 SiO$_2$, 1 Al$_2$O$_3$, 4.4 Na$_2$O, 6.2 TEA-chloride and 310 H$_2$O and was crystallized at 171° C. (340° F.), with stirring at 200 RPM, for 138 hours. The resultant TEA-mordenite was isolated by filtration, washed and dried and found to have a crystal size by scanning electron microscopy of >5 micron.

EXAMPLE 4

Transalkylation catalysts were produced from the zeolite materials produced in Examples 1–3 above by blending each with a 35% alumina binder and water and then extruding the blend into ¹⁄₁₆ inch cylindrical form. The extrudates were then precalcined in nitrogen at 540° C. (1000° F.) and subsequently ion exchanged with 1 N NH$_4$NO$_3$ and calcined in air at 540° C. (1000° F.) to convert the zeolites to the hydrogen form.

A mixture comprising benzene (150 g), diisopropyl benzene (50 g), and 8 g of the transalkylation catalyst produced from the small crystal TEA-mordenite of Example 1 was reacted in a Parr autoclave at 204° C. (400° F.), 2170 kPa (300 psig) and 300 rpm for 7 hr. A small sample of the product was withdrawn at 1,3,5, and 7 hours and analyzed by gas chromatography. The above test was repeated with the catalysts produced from the zeolites of Examples 2 and 3. The results of the three tests are summarised in Table 1, from which it will be seen that the catalyst of the invention was significantly more active than the prior art materials.

TABLE 1

| Reaction Time, hr | Wt % Diisopropylbenzene Conversion | | |
|---|---|---|---|
| | Example 1 | Example 2 | Example 3 |
| 1 | 54 | 0 | 5 |
| 3 | 84 | 24 | 14 |

What is claimed is:

1. A process for producing a monoalkylated aromatic compound comprising the steps of:
   (a) contacting an alkylatable aromatic compound with an alkylating agent in the presence of an alkylation catalyst in an alkylation reaction to provide a product comprising said monoalkylated aromatic compound and a polyalkylated aromatic compound, and then
   (b) contacting the polyalkylated aromatic compound from step (a) with said alkylatable aromatic compound in the liquid phase and in the presence of a transalkylation catalyst in a transalkylation reactor separate from said alkylation reactor, said transalkylation catalyst comprising TEA-mordenite having an average crystal size of less than 0.5 micron to produce said monoalkylated aromatic compound.

2. The process of claim 1, wherein the alkylation step (a) is conducted in the liquid phase.

3. The process of claim 1, wherein the alkylating agent includes an alkylating aliphatic group having 1 to 5 carbon atoms.

4. The process of claim 1, wherein the alkylating agent is ethylene or propylene and the alkylatable aromatic compound is benzene.

5. The process of claim 1, wherein the alkylation catalyst of step (a) is selected from MCM-22, MCM-49, MCM-56 and zeolite beta.

6. The process of claim 1, wherein step (a) is conducted at a temperature between about 300° and 600° F. (about 150° and 316° C.), a pressure up to about 3000 psig (20875 kPa), a space velocity between about 0.1 and 20 WHSV, based on the ethylene feed, and a ratio of the benzene to the ethylene between about 1:1 and 30:1 molar.

7. The process of claim 1, wherein step (b) is conducted at a temperature of 100 to 260° C., a pressure of 10 to 50 barg, a weight hourly space velocity of 1 to 10 on total feed, and benzene/polyalkylated benzene weight ratio 1:1 to 6:1.

8. The process of claim 1, wherein the TEA-mordenite was produced by crystallization from a synthesis mixture comprising a $Si/Al_2$ molar ratio of less than 90.

9. The process of claim 1, wherein the TEA-mordenite was produced by crystallization from a synthesis mixture comprising a $Si/Al_2$ molar ratio of between about 35 and about 50.

* * * * *